United States Patent [19]

Regan et al.

[11] 4,341,894

[45] Jul. 27, 1982

[54] SENSITIZERS FOR PHOTOCONDUCTIVE COMPOSITIONS

[75] Inventors: Michael T. Regan, Fairport; George A. Reynolds, Rochester; Donald P. Specht, Spencerport; James A. VanAllan, Rochester, all of N.Y.

[73] Assignee: Eastman Kodak Company, Rochester, N.Y.

[21] Appl. No.: 33,614

[22] Filed: Apr. 26, 1979

Related U.S. Application Data

[60] Division of Ser. No. 885,927, Mar. 13, 1978, Pat. No. 4,167,412, which is a continuation-in-part of Ser. No. 711,046, Aug. 2, 1976, abandoned.

[51] Int. Cl.[3] .................. C07D 309/32; C07D 335/00

[52] U.S. Cl. .................................. 544/333; 548/134; 548/136; 548/202; 546/268; 549/13; 549/29; 549/60; 549/213; 549/414; 548/405; 548/517; 548/524; 548/527

[58] Field of Search .................... 544/333; 260/345.1, 260/326.9, 345.9; 548/134, 136, 202; 546/268; 549/13, 29, 60

[56] References Cited

U.S. PATENT DOCUMENTS

| | | | |
|---|---|---|---|
| 3,615,396 | 10/1971 | Gramza et al. | 549/13 |
| 3,615,418 | 6/1969 | Standenmayer et al. | 96/1.5 |
| 3,679,406 | 7/1972 | Kryman | 549/13 |
| 3,679,408 | 7/1972 | Kryman et al. | 549/13 |
| 4,146,707 | 3/1979 | VanAllan et al. | 549/13 |

FOREIGN PATENT DOCUMENTS

| | | |
|---|---|---|
| 406832 | 9/1973 | U.S.S.R. . |
| 491628 | 11/1975 | U.S.S.R. . |

*Primary Examiner*—Nicholas S. Rizzo

*Attorney, Agent, or Firm*—Torger N. Dahl

[57] ABSTRACT

Sensitizers for photoconductive compositions and elements are disclosed. The sensitizers are 2,4,6 tri substituted pyrylium dye salts wherein at least one of said substituents is a 5 or 6 membered heterocyclic ring having at least one atom selected from the group consisting of N, O and S.

5 Claims, No Drawings

SENSITIZERS FOR PHOTOCONDUCTIVE COMPOSITIONS

This is a division of application Ser. No. 885,927, filed Mar. 13, 1978, now U.S. Pat. No. 4,167,412, which is a continuation-in-part application of U.S. Ser. No. 711,046 filed Aug. 2, 1976, now abandoned.

FIELD OF THE INVENTION

This invention relates to a novel class of heterocyclic pyrylium dye salts and in particular to the utility of such dye salts in photoconductive composition and elements.

BACKGROUND OF THE INVENTION

Electrophotographic imaging processes and techniques have been extensively described in both the patent and other literature, for example, U.S. Pat. Nos. 2,221,776; 2,277,013; 2,297,691; 2,357,809; 2,551,582; 2,825,814; 2,833,648; 3,220,324; 3,220,831; 3,220,833 and many others. Generally, these processes have in common the steps of employing a photoconductive insulating element which is prepared to respond to imagewise exposure with electromagnetic radiation by forming a latent electrostatic charge image. A variety of subsequent operations, now well known in the art, can then be employed to produce a permanent record of the image.

One type of photoconductive insulating element particularly useful in electrophotography employs a composition containing a photoconductive insulating material and optionally an electrically insulating film-forming resinous binder material. A unitary electrophotographic element incorporating such a composition is generally produced in a multilayer type of structure by coating a layer of the above-described composition onto a support previously overcoated with a layer of a conducting material. Alternatively, the above-described composition can be coated directly onto a conductive support of metal or other suitable conductive material.

Although many organic photoconductor materials are inherently light sensitive, their degree of sensitivity is frequently so low that it is often desirable to improve the speed and/or spectral response of photoconductive compositions generally employed in electrophotographic processes by incorporating in such compositions various sensitizer materials and addenda. Among the various sensitizer addenda which have been found especially effective for use in photoconductive compositions are the dyes selected from the group consisting of pyrylium, selenapyrylium, and thiapyrylium dye salts such as are disclosed in U.S. Pat. Nos. 3,250,615; 3,141,770; 3,679,408; and 3,615,418. Generally, the aforementioned pyrylium, thiapyrylium, and selenapyrylium dye salts heretofore used in photoconductive compositions have been found effective to change the sensitivity or electrical speed of a particular photoconductive composition. Although the mechanism of such sensitization is presently not fully understood, the phenomenon has been found extremely useful.

The importance of such effects is evidenced by the extensive search currently conducted by workers in the art for compositions and compounds which are capable of photosensitizing photoconductive compositions in the manner described.

Usually the desirability of a change in electrophotographic properties is dictated by the end use contemplated for the photoconductive element. For example, in document copying applications the spectral electrophotographic response of the photoconductor should be capable of reproducing the wide range of colors which is normally encountered in such use. If the response of the photoconductor falls short of these design criteria, it is highly desirable if the spectral response of the composition can be altered by the addition of photosensitizing addenda to the composition. Likewise, various applications specifically require other characteristics such as the ability of the element to accept a high surface potential, and exhibit a low dark decay of electrical charge.

It is also desirable for the photoconductive element to exhibit high speed as defined by an electrical speed measurement or a characteristic electrical discharge curve, a low residual potential after exposure and resistance to fatigue. Sensitization of many photoconductive compositions by the addition of certain dyes selected from the large number of dyes presently known has hitherto been widely used to provide for the desired flexibility in the design of photoconductive elements. Conventional dye addenda to photoconductor compositions have generally shown only a limited capability for overall improvement in the totality of electrophotographic properties which cooperate to produce a useful electrophotographic element or structure. The art is still searching for improvements in spectral sensitivity, shoulder and toe speeds, improved solid area reproduction characteristics, rapid recovery and useful electrophotographic shoulder and toe speeds with either positive or negative electrostatic charging.

A high speed "heterogeneous" or "aggregate" photoconductive system has been developed which overcomes many of the problems of the prior art. This aggregate composition and certain components thereof are the subject matter of William A. Light, U.S. Pat. No. 3,615,414 issued Oct. 26, 1971 and Gramza et al. U.S. Pat. No. 3,732,180 issued May 8, 1973. The addenda disclosed therein are responsible for the exhibition of desirable electrophotographic properties in photoconductive elements prepared therewith. However, use of the pyrylium type sensitizing dyes described therein quite often results in an aggregate photoconductive element which does not exhibit a panchromatic response throughout the visible spectrum. For example, some elements exhibit an absorption minimum (and therefore a somewhat lower sensitivity than would be desired) to light in some portion of the visible spectrum, for example, in the blue region of the spectrum, i.e. light having a wavelength within the range of from about 400 to about 500 nm. Other such elements exhibit an absorption maximum in a region near the long wavelength boundry of the visible spectrum resulting in less useful sensitivity than desired within the visible spectrum. Accordingly, there is a need in the art for high speed aggregate photoconductive compositions having improved panchromatic sensitivity as well as the means for selectively modifying high speed aggregate photoconductive compositions to obtain spectral response in those regions of the electromagnetic spectrum where the aggregate composition exhibits somewhat lower or higher absorption than is desired.

SUMMARY OF THE INVENTION

We have discovered that 2,4,6-trisubstituted pyrylium dye salts, having at least one heterocyclic substituents of the type described herein below are useful in improving the electrophotographic response of photoconductive insulating compositions. Said 2,4,6-trisubstituted pyrylium dye salts are sometimes referred to hereinafter as heterocyclic pyrylium dye salts. Both expressions are defined herein to include heterocyclic pyrylium and thiopyrylium dye salts.

According to one embodiment of the present invention, said heterocyclic pyrylium dye salts are useful in spectrally sensitizing homogeneous organic photoconductive insulating compositions, particularly to the visible portions of the spectrum. By homogeneous photoconductive insulating compositions is meant a photoconductive composition that is substantially clear and free of any particulate matter as observed at or up to 2500x magnification.

According to another embodiment of the present invention, said heterocyclic pyrylium dye salts are useful in (1) selectively modifying the absorption and sensitivity of conventional high speed aggregate photoconductive compositions to obtain the desired absorption in those areas of the visible spectrum that a particular design criteria might dictate and/or (2) improving the panchromatic response of conventional high speed aggregate photoconductive compositions.

DESCRIPTION OF PREFERRED EMBODIMENTS

The 2,4,6-trisubstituted pyrylium dye salts of the present invention have at least one heterocyclic substituent, said heterocyclic substituent being a 5 to 6 member ring having at least one atom selected from the group consisting of N, O or S provided that said heterocyclic substituent is other than pyrylium or thiopyrylium.

Particularly useful heterocyclic pyrylium dye salts of the present invention have the general formula:

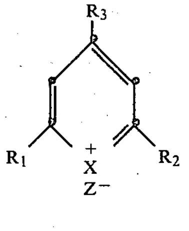

(I)

in which $R_1$ and $R_2$ represent a phenyl radical, including substituted phenyl radicals, thienyl, furyl, pyridyl, pyrimidinyl, thiadiazolyl or thiazolyl or pyrrolyl; $R_3$ represents an alkylamino-substituted phenyl radical having from 1 to 6 carbon atoms in the alkyl moiety including dialkylamino-substituted and halogenated alkylamino-substituted phenyl radicals, dialkyaminopyridyl, dialkylaminofuryl, dialkylaminothienyl, dialkylaminopyrimidinyl, dialkylaminothiadiazolyl or dialkylaminothiazolyl; X is oxygen or sulfur and Z is an anion and wherein at least one of $R_1$, $R_2$ and $R_3$ is one of the above enumerated heterocyclic moieties. Typical compounds included within the above formula are set out in Table I.

TABLE I

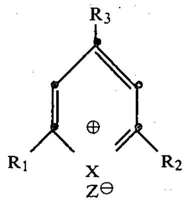

| Example Number | $R^1$ | $R^2$ | $R^3$ | $X^{\oplus}$ | $Z^{\ominus}$ |
|---|---|---|---|---|---|
| 1 | Phenyl | 3-Pyridyl | 4-Dimethylamino-phenyl | O | $ClO_4^{\ominus}$ |
| 2 | Phenyl | Phenyl | 6-Dimethylamino-3-pyridyl | O | $ClO_4^{\ominus}$ |
| 3 | Phenyl | 2-Thienyl | 4-Dimethylamino-phenyl | O | $ClO_4^{\ominus}$ |
| 4 | 3-Pyridyl | 3-Pyridyl | 4-Dimethylamino-phenyl | O | $ClO_4^{\ominus}$ |
| 5 | 2-Thienyl | 4-Pyridyl | 4-Dimethylamino-phenyl | O | $ClO_4^{\ominus}$ |
| 6 | 2-Thienyl | 2-Pyridyl | 4-Dimethylamino-phenyl | O | $ClO_4^{\ominus}$ |
| 7 | Phenyl | 2-Pyridyl | 4-Dimethylamino-phenyl | O | $ClO_4^{\ominus}$ |
| 8 | Phenyl | 2-Furyl | 4-Dimethylamino-phenyl | O | $ClO_4^{\ominus}$ |
| 9 | 2-Thienyl | 2-Furyl | 4-Dimethylamino-phenyl | O | $ClO_4^{\ominus}$ |
| 10 | Phenyl | 3-Pyridyl | 4-Dimethylamino-phenyl | S | $ClO_4^{\ominus}$ |
| 11 | 3-Pyridyl | 3-Pyridyl | 4-Dimethylamino-phenyl | S | $ClO_4^{\ominus}$ |
| 12 | Phenyl | 2-Thienyl | 4-Dimethylamino-phenyl | S | $ClO_4^{\ominus}$ |
| 13 | Phenyl | Phenyl | 6-Dimethylamino-3-pyridyl | S | $ClO_4^{\ominus}$ |
| 14 | 2-Thienyl | 3-Pyridyl | 4-Dimethylamino-phenyl | S | $ClO_4^{\ominus}$ |
| 15 | 2-Thienyl | 4-Pyridyl | 4-Dimethylamino-phenyl | S | $ClO_4^{\ominus}$ |
| 16 | 2-Thienyl | 2-Pyridyl | 4-Dimethylamino-phenyl | S | $ClO_4^{\ominus}$ |
| 17 | Phenyl | 2-Pyridyl | 4-Dimethylamino-phenyl | S | $ClO_4^{\ominus}$ |
| 18 | Phenyl | 2-Furyl | 4-Dimethylamino-phenyl | S | $ClO_4^{\ominus}$ |
| 19 | 2-Thienyl | 2-Thienyl | 4-Dimethylamino-phenyl | S | $BF_4^{\ominus}$ |
| 20 | Phenyl | 2-Thienyl | 4-Dimethylamino-phenyl | S | $BF_4^{\ominus}$ |
| 21 | Phenyl | 2-Thienyl | 4-Dimethylamino-phenyl | O | $PF_6^{\ominus}$ |
| 22 | Phenyl | 2-Thienyl | 4-Dimethylamino-phenyl | S | $PF_6^{\ominus}$ |
| 23 | 2-Furyl | 2-Furyl | 4-Dimethylamino-phenyl | O | $ClO_4^{\ominus}$ |
| 24 | 2-Furyl | 2-Furyl | 4-Dimethylamino-phenyl | S | $ClO_4^{\ominus}$ |
| 25 | 3-Thienyl | 2-Thienyl | 4-Dimethylamino-phenyl | S | $ClO_4^{\ominus}$ |
| 26 | 2-Thienyl | 2-Thienyl | 4-Dimethylamino-phenyl | S | $ClO_4^{\ominus}$ |
| 27 | 2-Thienyl | 2-Thienyl | 4-Dimethylamino-phenyl | O | $ClO_4^{\ominus}$ |
| 28 | 2-Pyrimi-dinyl | Phenyl | 4-Dimethylamino-phenyl | S | $ClO_4^{\ominus}$ |
| 29 | Phenyl | 1,3,4-Thia-diazol-2-yl | 4-Dimethylamino-phenyl | S | $ClO_4^{\ominus}$ |
| 30 | Phenyl | 2-Thiazolyl | 4-Dimethylamino-phenyl | S | $ClO_4^{\ominus}$ |
| 31 | Phenyl | Phenyl | 5-Dimethylamino-2-thienyl | S | $ClO_4^{\ominus}$ |
| 32 | 3-Pyridyl | Phenyl | 4-dimethylamino-phenyl | S | $ClO_4^{\ominus}$ |

The compounds of the present invention can be prepared in accordance with the following reaction scheme:

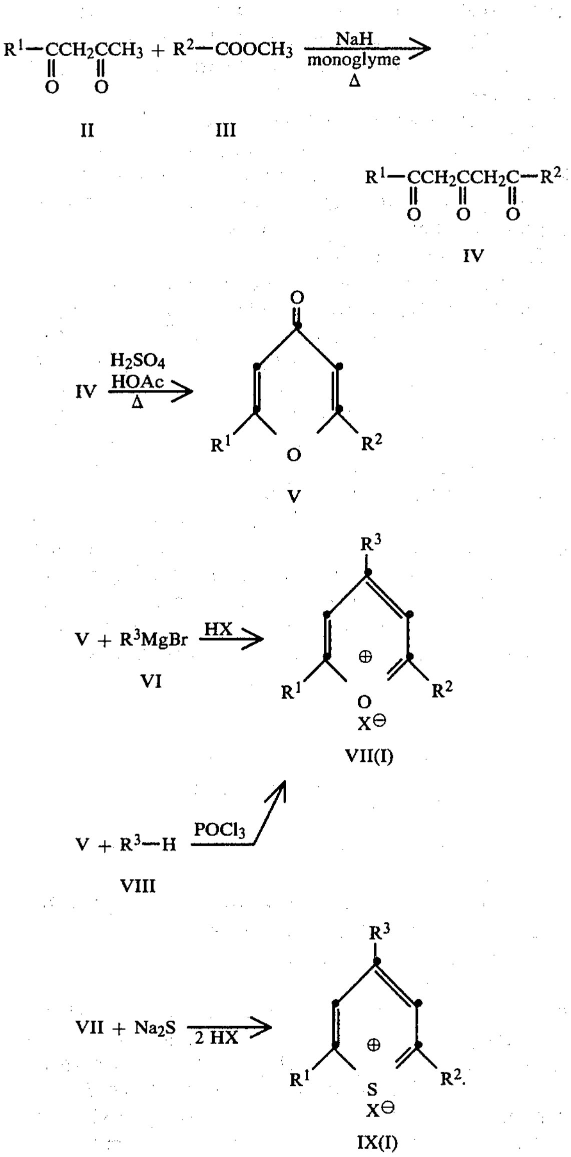

II III IV V VI VII(I) VIII IX(I)

The following compound preparations further illustrate the general reaction scheme.

Preparation of triketones: A mixture of 20 g (0.47 mole) of 57% sodium hydride in mineral oil and 150 ml of dry monoglyme heated at reflux under nitrogen and a mixture of 0.1 mole of the methyl ester and 0.1 mole of the diketone (II) (or 0.1 mole of acetone and 0.2 mole of the methyl ester (III) is added dropwise with stirring. The mixture was stirred and refluxed for 4 hrs, the solvent removed under vacuum, and the chilled residue treated with 250 ml of water (in some cases more water is added so that a solution is obtained). The solution is extracted with ether, and the aqueous phase is neutralized with acetic acid. The solid is collected, washed with water and recrystallized from alcohol.

Preparation of Pyrones: A mixture of 0.05 mole of the triketone, 20 ml of sulfuric acid and 100 ml of acetic acid is heated for one hour on a steam bath, cooled and added to 200 ml of water and the solid is collected. The compounds which contained pyridyl groups yield salts under these conditions which either precipitate or are obtained as the free base by neutralizations of the reaction mixture with sodium carbonate. The crude pyrones are recrystallized from alcohol.

Preparation of Hetercyclic Pyrylium Salts: A solution of 0.018 mole of the pyrone in 75 ml of dry tetrahydrofuran is added to a stirred solution of 0.02 mole of p-dimethylaminophenyl magnesium bromide in 50 ml of tetrahydrofuran. The Grignard reagent is prepared by boiling 0.02 mole of magnesium and 0.02 mole of p-bromodimethylaniline in 50 ml of THF until a clear solution is obtained (about 1 hr). The reaction mixture is refluxed with stirring under nitrogen for 2 hrs, cooled and poured into dilute aqueous perchloric acid (or other acids such as fluoroboric or $HPF_6$ when other anions are desired). The solid is collected and recrystallized from acetonitrile. In compounds containing pyridyl groups, bisperchlorate salts are obtained which are dissolved in pyridine and the solution diluted with alcohol giving the mono perchlorate salt.

Alternately, the heterocyclic pyrylium dye salt may be prepared by heating a mixture of 0.05 moles of the pyrone, 50 ml of phosphoryl chloride and 0.1 mole of dimethylaniline on a steam bath for 2 hrs, cooling and diluting with ether The solid is collected, dissolved in hot alcohol and 0.05 moles of 70% perchloric acid was added. After cooling the mixture the solid is collected and recrystallized from acetonitrile.

Preparation of Heterocyclic Thiopyrylium Salts: A suspension of 0.01 mole of the pyrylium salt in 100 ml of acetone was stirred with 2 g of sodium sulfide in 50 ml of water for 30 minutes. The red solution was poured into dilute aqueous perchloric acid ($HBF_4$ and $HPF_6$ can also be used). The solid was collected and recrystallized from acetonitrile.

Preparation of 4-(2-Dimethylamino-5-pyridyl)-2,6-diphenylthiopyrylium perchlorate: A mixture of 10 g of 5-bromo-2-dimethylaminopyridine, 1.2 g of magnesium and 75 ml of dry THF is refluxed under nitrogen for an hour. A white solid precipitates. To the mixture is added 10 g of 2,6-diphenyl-4H-pyran-4-one and the heating is continued for 2 hrs. The clear solution is poured into cold dilute perchloric acid, and the solid is collected and washed with water. The solid is a mixture of red and yellow compounds. The yellow material is removed by extraction with hot alcohol, and the red product is recrystallized from acetonitrile using a Soxhlet extractor giving 5 g of 4-(2-dimethylamino-5-pyridyl)-2,6-diphenylpyrylium perchlorate, Mp 355° C.

A mixture of 4 g of the pyrylium salt in 100 ml of acetone was stirred and 2 g of sodium sulfide in 50 ml of water is added. The solution was stirred for ½ hr and poured into dilute perchloric acid. The solid (which was the bis perchlorate salt) was dissolved in pyridine, the solution was diluted with alcohol and the solid which separated was collected, Mp 271°–272°, yield 3 g. The λmax ($CH_3CN$) were 550 ($58.0\times10^3$), ~280 ($17.0\times10^3$) and 265 nm ($18.0\times10^3$).

Other compounds having heterocyclic $R_3$ substituents may be similarly prepared.

As previously stated the heterocyclic pyrylium dye salts of the present invention are useful as sensitizers in aggregate photoconductive insulating compositions. Such compositions may comprise in addition to at least one heterocyclic pyrylium dye salt of the present invention, an electrically insulating, film-forming polymeric material, an organic photoconductor and/or one or more of the conventional pyrylium dye salts such as those utilized in Light, U.S. Pat. No. 3,615,414.

Such aggregate photoconductive insulating compositions may be prepared by several techniques, such as, for example, the so-called "shearing" technique described in Gramza et al U.S. Pat. No. 3,615,415 issued Oct. 26, 1971. This latter method involves the high speed shearing of the photoconductive composition prior to coating and thus eliminates subsequent solvent treatment, as was disclosed in Light, U.S. Pat. No. 3,615,414 referred to above. By whatever method prepared, the resulting aggregate composition is combined with a suitable solvent to form a coating composition which is self-supporting or is alternately coated on a suitable support to form a separately identifiable multiphase composition, the aggregate nature of which is generally apparent when viewed under magnification, although such compositions may appear to be substantially optically clear to the naked eye in the absence of magnification. There can, of course, be macroscopic heterogeneity. Suitably, the dye-containing aggregate in the discontinuous phase is predominantly in the size range of from about 0.01 to about 25 microns.

Supplemental materials useful for changing the spectral sensitivity or electrophotosensitivity of the element can be added to the composition of the element when it is desirable to produce the characteristic effect of such materials. If desired, other polymers can be incorporated in the vehicle, for example, to alter physical properties such as adhesion of the photoconductive layer to the support and the like. Techniques for the preparation of aggregate photoconductive layers containing such additional vehicles are described in C. L. Stephens, U.S. Pat. No. 3,670,407 issued July 25, 1972, and entitled METHOD OF FORMING HETEROGENEOUS PHOTOCONDUCTIVE COMPOSITIONS AND ELEMENTS. The photoconductive layers of the invention can also be sensitized by the addition of effective amounts of sensitizing compounds to exhibit improved electrophotosensitivity.

In general, the aggregate compositions formed as described herein are multiphase organic solids containing dye salt and polymer. The polymer forms an amorphous matrix or continuous phase which contains a discrete discontinuous phase as distinguished from a solution. The discontinuous phase is the aggregate species which is a co-crystalline complex comprised of at least one heterocyclic pyrylium dye salt and polymer. The continuous phase can contain an organic photoconductor.

The term co-crystalline complex as used herein has reference to a crystalline compound which contains dye and polymer molecules co-crystallized in a single crystalline structure to form a regular array of the molecules in a three-dimensional pattern. This co-crystalline complex containing the heterocyclic dye salts of the present invention may be employed by itself as a photoconductor in a heterogeneous or aggregate photoconductive composition. Or said co-crystalline complex may be used as a sensitizer addenda for other photoconductive compositions.

Another feature characteristic of the aggregate compositions formed as described herein is that the wavelength of the radiation adsorption maximum characteristic of such compositions is substantially shifted from the wavelength of the radiation absorption maximum of a substantially homogeneous dye-polymer solid solution formed of similar constituents. The new absorption maximum characteristic of the aggregates formed by this method is not necessarily an overall maximum for this system as this will depend upon the relative amount of dye in the aggregate. Such an absorption maximum shift in the formation of aggregate systems for the present invention is generally of the magnitude of at least about 10 nm. If mixtures of dyes are used, one dye may cause an absorption maximum shift to a longer wavelength and another dye cause an absorption maximum shift to a shorter wavelength. In such cases, a formation of the aggregate compositions can more easily be identified by viewing under magnification.

The heterocyclic pyrylium dye salts of the present invention are useful in enhancing the sensitivity of a wide variety of organic photoconductors used in aggregate photoconductive compositions. Typical organic photoconductors are those disclosed herein below are being useful photoconductors for non-aggregate or homogeneous photoconductive insulating compositions. Such organic photoconductors are typically utilized in the continuous phase of aggregate photoconductive insulating compositions.

The polymers useful in forming the aggregate compositions include a variety of materials. Particularly useful are electrically insulating, film-forming polymers having an alkylidene diarylene group in a recurring unit such as those linear polymers, including copolymers, containing the following group in a recurring unit:

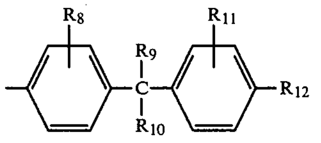

wherein:

$R_9$ and $R_{10}$, when taken separately, can each be a hydrogen atom, an alkyl group having from one to about 10 carbon atoms such as methyl, ethyl, isobutyl, hexyl, heptyl, octyl, nonyl, decyl, and the like including substituted alkyl groups such as trifluoromethyl, etc., and an aryl group such as phenyl and naphthyl, including substituted aryl groups having such sutstituents as a halogen atom, an alkyl group of from 1 to about 5 carbon atoms, etc.; and $R_9$ and $R_{10}$, when taken together, can represent the carbon atoms necessary to complete a saturated cyclic hydrocarbon group including cycloalkanes such a cyclohexyl and polycycloalkanes such as norbornyl, the total number of carbon atoms in $R_9$ and $R_{10}$ being up to about 19.

$R_8$ and $R_{11}$ can each be hydrogen, an alkyl group of from 1 to about 5 carbon atoms, e.g., or a halogen such as chloro, bromo, iodo, etc.; and $R_{12}$ is a divalent group selected from the following:

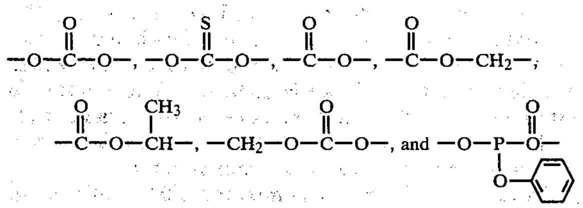

Preferred polymers useful for forming aggregate crystals are hydrophobic carbonate polymers containing the following group in a recurring unit:

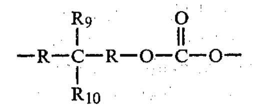

wherein:

each R is a phenylene group including halo substituted phenylene groups and alkyl substituted phenylene groups; and $R_9$ and $R_{10}$ are described above. Such compositions are disclosed, for example in U.S. Pat. Nos. 3,028,365 and 3,317,466. Preferable polycarbonates containing an alkylidene diarylene group in the recurring unit such as those prepared with Bisphenol A and including polymeric products of ester exchange between diphenylcarbonate and 2,2-bis-(4-hydroxyphenyl) propane are useful in the practice of this invention. Such compositions are disclosed in the following U.S. Patents: No. 2,999,750 by Miller et al, issued Sept. 12, 1961; No. 3,038,874 by Laakso et al, issued June 12, 1962; No. 3,038,879 by Laakso et al, issued June 12, 1962; No. 3,038,880 by Laakso et al, issued June 12, 1962; No. 3,106,544 by Laakso et al, issued Oct. 8, 1963; and No. 3,106,545 by Laakso et al, issued Oct. 8, 1963; and No. 3,106,546 by Laakso et al, issued Oct. 8, 1963. A wide range of film-forming polycarbonate resins are useful, with completely satisfactory results being obtained when using commercial polymeric materials which are characterized by an inherent viscosity of about 0.5 to about 1.8.

The following polymers are included among the materials useful in forming the aggregate compositions of the present invention:

TABLE 2

| No. | Polymeric Material |
|---|---|
| 1 | poly(4,4'-isopropylidenediphenylene-co-1,4-cyclohexylenedimethylene carbonate) |
| 2 | poly (ethylenedioxy-3,3'-phenylene thiocarbonate) |
| 3 | poly(4,4'-isopropylidenediphenylene carbonate-co-terephthalate) |
| 4 | poly(4,4'-isopropylidenediphenylene carbonate) |
| 5 | poly(4,4'isopropylidenediphenylene thiocarbonate) |
| 6 | poly(4,4'-sec-butylidenediphenylene carbonate) |
| 7 | poly(4,4'-isopropylidenediphenylene carbonate-block-oxyethylene) |
| 8 | poly(4,4'-isopropylidenediphenylene carbonate-block-oxytetramethylene) |
| 9 | poly[4,4'-isopropylidenebis(2-methylphenylene) carbonate] |
| 10 | poly(4,4'-isopropylidenediphenylene-co-1,4-phenylene carbonate) |
| 11 | poly(4,4'-isopropylidenediphenylene-co-1,3-phenylene carbonate) |
| 12 | poly(4,4'-isopropylidenediphenylene-co-4,4'-diphenylene carbonate) |
| 13 | poly(4,4'-isopropylidenediphenylene-co-4,4'-oxydiphenylene carbonate) |
| 14 | poly(4,4'-isopropylidenediphenylene-co-4,4'-carbonyldiphenylene carbonate) |
| 15 | poly(4,4'-isopropylidenediphenylene-co-4,4'-ethylenediphenylene carbonate) |
| 16 | poly[4,4'-methylenebis(2-methylphenylene)carbonate] |
| 17 | poly[1,1-(p-bromophenylethylidene)bis(1,4-phenylene)carbonate] |
| 18 | poly[4,4'-isopropylidenediphenylene-co-4,4'-sulfonylidiphenylene)carbonate] |
| 19 | poly[4,4'-cyclohexylidene(4-diphenylene) carbonate] |
| 20 | poly[4,4'-isopropylidenebis(2-chlorophenylene)carbonate] |
| 21 | poly(4,4'-hexafluoroisopropylidenediphenylene carbonate) |
| 22 | poly(4,4'-isopropylidenediphenylene 4,4'-isopropylidenedibenzoate) |
| 23 | poly (4,4'-isopropylidenedibenzyl 4,4'-isopropylidenedibenzoate) |
| 24 | poly 4,4'-[1-(α-naphthyl)ethylidene] -diphenylene carbonate] |
| 25 | poly[4,4'-(2-norbornylidene)diphenylene carbonate] |
| 26 | poly[4,4'-(hexahydro-4,7-methanoindan-5-ylidene)diphenylene carbonate] |

The amount of the heterocyclic pyrylium dye incorporated into aggregate photoconductive compositions and elements can be varied over a relatively wide range. When used in an aggregate photoconductive composition, substantially all heterocyclic pyrylium dye salts described herein or a mixture thereof should, preferably, be in the discontinuous phase of the aggregate composition. When such compositions are used as photoconductive compositions the dye salts may be present in an amount of about the range of from about 1.0 to about 50.0 percent by weight of the coating composition. Larger or smaller amounts of the heterocyclic pyrylium dye salts may also be employed in aggregate photoconductive compositions although best results are generally obtained when using an amount within the aforementioned range. When such aggregate compositions are used as sensitizers for photoconductive coatings, useful results are obtained by using the heterocyclic pyrylium dye salts in amounts of about 0.001 to about 30 percent by weight of the photoconductive coating compositions, although the amount used can be widely varied. The upper limit in the amount of photoconductive compositions present in a sensitized layer is determined as a matter of individual choice and the total amount of any photoconductor used will vary widely depending on the material selected, the electrophotographic response desired, the proposed structure of the photoconductive element and the mechanical properties desired in the element. Lesser amounts of the present feature compositions can be utilized as sensitizing amounts to increase the speed sensititivity of other photoconductors than amounts that would be used if the feature material were the only sensitizer present. The amount of sensitizer in the coated composition on a dry basis can also vary widely. In general, acceptable sensitizer coverage usually falls in the range of about 0.5 mg to about 1000 mg per square foot, preferably 5.0 mg to 300 mg per square foot. It is appreciated, however, that coverages outside of these ranges can also be effective.

As stated before according to one embodiment of the present invention, the heterocyclic pyrylium dye salts of the present invention are useful in improving the spectral response of organic photocoductive insulating compositions and elements. For example, an homogeneous organic photoconductive insulating composition comprising a solid solution of at least one of the heterocyclic pyrylium dye salt of the present invention and a polymeric binder exhibit improved sensitivity in the visible portion of the spectrum.

The organic photoconductive insulating compositions in which the compounds of the present invention are used are essentially organic material-containing compositions free from all inorganic photoconductors, such as zinc oxide. The term "organic" as used herein refers to both organic and metallo-organic materials.

Such organic photoconductive insulating compositions can be prepared with a variety of organic photoconductive compounds and the spectral sensitizing compounds of this invention in the usual manner, i.e., by blending a dispersion or solution of the organic photoconductive compound together with an electrically insulating, film-forming resin binder when necessary or desirable and coating or forming a self-supporting layer with the photoconductive composition. Generally, a suitable amount of the sensitizing compound is mixed with the photoconductive coating composition so that after thorough mixing, the sensitizing compound is uniformly distributed throughout the desired layer of the coated element. The amount of sensitizer that can be added to an organic photoconductor-containing layer to give effective spectral sensitization can vary widely. The optimum concentration in any given case will vary with the specific organic photoconductor and sensitizing compound used. In general, a sensitizer of the present invention is added in a concentration range from about 0.001 to about 30 percent by weight based on the weight of the film-forming coating composition. Normally, the sensitizer is added to the coating composition in an amount from about 0.005 to about 10 percent by weight of the total coating composition. The amount of sensitizer in the coated composition on a dry basis can also vary widely. In general, acceptable sensitizer coverage usually falls in the range of about 0.5 mg to about 1000 mg per square foot, preferably 5.0 mg to 300 mg per square foot. It is appreciated, however, that coverages outside of these ranges can also be effective.

The heterocyclic pyrylium dye salts of the present invention are useful in enhancing the sensitivity of a wide variety of photoconductors including inorganic and organic photoconductors such as those disclosed in Research Disclosure Vol. 109, page 62 (May, 1973). Such photoconductors are useful in both aggregate and homogeneous photoconductive insulating compositions. The compounds of the present invention are particularly useful for sensitizing organic photoconductors.

Preferred binders for use in preparing the spectrally sensitized homogeneous photoconductive layers according to the present invention comprise electrically insulating film forming polymers having a fairly high dielectric strength. Materials of this type comprise styrene-butadiene copolymers; silicone resins; styrene-alkyd resins; silicone alkyd resins; soya-alkyd resins; poly(vinyl chloride); poly(vinylidene chloride); vinylidene chloride-acrylonitrile copolymers; poly (vinyl acetate); vinyl acetate-vinyl chloride copolymers; poly (vinyl acetals), such as poly(vinyl butyral); polyacrylic and methacrylic esters, such as poly(methyl methacrylate), poly (n-butyl methacrylate), poly(isobutyl methacrylate), etc.; polystyrene; nitrated polystyrene; poly(-methylstyrene); isobutylene polymers; polyesters, such as poly(ethylene alkaryloxyalkylene terephthalate), phenol-formaldehyde resins; ketone-resins; polyamides; polycarbonates; polythiocarbonates; poly-[ethyleneglycol-co-bis(hydroxyethoxyphenyl)propane terephthalate]; nuclear substituted poly(vinyl haloarylates); etc. Methods of making resins of this type have been described in the prior art, for example, styrenealkyd resins can be prepared according to the method described in U.S. Pat. Nos. 2,361,019 and 2,258,423. Suitable resins of the type contemplated for use in the photoconductive layers of the invention are sold under such trademarks as Vitel PE-101, Cymac, Piccopale 100, Saran F-220 and Lexan 105 and 145. Other types of binders which can be used in the photoconductive layers of the invention include such materials as paraffin, mineral waxes, etc. If a polymeric photoconductor is used, the binder may be omitted altogether.

The organic coating solvents useful for preparing spectrally sensitized homogeneous photoconductive coating dopes can be selected from a variety of materials. Useful liquids are hydrocarbon solvents, including substituted hydrocarbon solvents, with preferred materials being halogenated hydrocarbon solvents. The requisite properties of the solvent are that it be capable of dissolving the pyrylium dye and be capable of dissolving or at least highly swelling or solubilizing the polymeric ingredient of the composition. In addition, it is helpful if the solvent is volatile, preferably having a boiling point of less than about 200° C. Particularly useful solvents include halogenated lower alkanes having from 1 to about 3 carbon atoms, such as dichloromethane, dichloroethane, dichloropropane, trichloromethane, trichloroethane, tribromomethane, trichloromonofluoromethane, trichlorotrifluoroethane, etc.; aromatic hydrocarbons such as benzene, toluene as well as halogenated benzene compounds such as chlorobenzene, bromobenzene, dichlorobenzene, etc.; ketones such as dialkyl ketones having 1 to about 3 carbon atoms in the alkyl moiety such as acetone, methyl ethyl ketone, etc.; and ethers such as tetrahydrofuran, etc. Mixtures of these and other solvents can also be used.

In preparing the homogeneous organic photoconductive insulating coating composition, useful results are obtained where the organic photoconductor is present in an amount equal to at least about 1 weight percent of the coating composition. The upper limit in the amount of photoconductor substance present can be widely varied in accordance with usual practice. In those cases where a binder is employed, it is normally required that the photoconductor substance is normally present in an amount from about 1 weight percent of the coating composition to about 99 weight percent of the coating composition. A polymeric photoconductor may be employed in which case an additional binder may not be required, A preferred weight range for the organic photoconductor substance in the coating composition is from about 10 weight percent to about 60 weight percent.

Suitable supporting materials for both the aggregate and homogeneous photoconductive layers produced in accordance with the present invention can include any of a wide variety of electrically conducting support, for example, paper (at a relative humidity above 20 percent); aluminum-paper laminates; metal foils such as aluminum foil, zinc foil, etc; metal plates such as aluminum, copper, zinc, brass and galvanized plates; vapor-deposited metal layers such as silver, chromium, nickel, aluminum, cermet materials and the like coated on paper or conventional photographic film bases such as cellulose acetate, polystyrene, etc. Such conducting materials as nickel can be vacuum deposited on transparent film supports in sufficiently thin layers to allow electrophotographic elements prepared therewith to be exposed from either side of such elements. An especially useful conducting support can be prepared by coating a support material such as poly(ethylene terephthalate) with a conducting layer containing a semiconductor dispersed in a resin. Such conducting layers both with and without insulating barrier layers are described in U.S. Pat. Nos. (3,245,833) and 3,880,657. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 and 3,262,807.

Coating thicknesses of the photoconductive composition on the support can vary widely. Normally, a coating in the range of about 10 microns to about 300 microns before drying is useful for the practice of this invention. The preferred range of coating thickness is found to be in the range from about 50 microns to about 150 microns before drying, although useful results can be obtained outside of this range. The resultant dry thickness of the coating is preferably between about 2 microns and about 50 microns, although useful results can be obtained with a dry coating thickness between about 1 and about 200 microns.

The elements of the present invention can be employed in any of the well-known electrophotographic processes which require photoconductive layers. One such process is the xerographic process. In a process of this type, an electrophotographic element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by image-wise exposure to light by means of a conventional exposure operation such as, for example, by a contact-printing technique, or by projection of an image, and the like, to thereby form a latent electrostatic image in the photoconductive layer. Exposing the surface in this manner forms a pattern of electrostatic charge by virtue of the fact that light energy striking the photoconductor causes the electrostatic charge in the light struck areas to be conducted away from the surface in proportion to the intensity of the illumination of a particular area.

The charge pattern produced by exposure is then developed or transferred to another surface and developed there, i.e., either the charge or uncharged areas are rendered visible, by treatment with a medium comprising electrostatically responsive particles having optical density. The developing electrostatically responsive particles can be in the form of dust, i.e., powder, or a pigment in a resinous carrier, i.e., toner. A preferred method of applying such toner to a latent electrostatic image for solid area development is by the use of a magnetic brush. Methods of forming and using a magnetic brush toner applicator are described in the following U.S. Patents: Young No. 2,786,439 issued Mar. 26, 1957; Giaimo No. 2,786,440 issued Mar. 26, 1957; Young No. 2,786,441 issued Mar. 26, 1957; Greig No. 2,874,063 issued Feb. 17, 1959. Liquid development of the latent electrostatic image may also be used. In liquid development, the developing particles are carried to the image-bearing surface in an electrically insulating liquid carrier. Methods of development of this type are widely known and have been described in the patent literature, for example, Metcalfe et al U.S. Pat. No. 2,907,674 issued Oct. 6, 1959. In dry developing processes, the most widely used method of obtaining a permanent record is achieved by utilizing a developing particle which has as one of its components a thermoplastic resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer can be made to a second support.

The following examples are included for a further understanding of the inventor.

EXAMPLE 1

A series of photoconductive compositions containing one of the following photoconductors:

A. triphenylamine

B. 4,4′-bis(diethylamino)-2,2′-dimethyltriphenyl methane as the photoconductive material were prepared for coating on a conducting support material by mixing 0.25 parts of the photoconductor with 0.01 parts by weight of compounds 12, 17, 18, 20 and 25 of Table I as sensitizer and dissolving the mixture, together with 1.0 parts by weight of a resinous polyester binder, by stirring in dichloromethane. The resultant mixture was then hand coated over a polymeric carboxy ester lactone layer carried on a transparent support. In all instances, the polyester binder in the coating composition is Vitel PE-101 (trademark of Goodyear Tire and Rubber Co.) and is believed to be poly (4,4′-isopropylidenebis(phenylene oxyethylene)-co-ethylene terephthalate) 50/50. The wet coating thickness on the support was 0.1 mm. After drying, a sample of each electrophotographic element was employed in a standard xerographic process to determine the relative speed thereof. For comparison, photoconductors A and B employed in the photoconductive compositions used to obtain the data shown in Table 3 were evaluated in samples containing no sensitizer.

The relative speed measurements reported in this and the following examples are relative H & D electrical speeds. The relative H & D electrical speeds measure the speed of a given photoconductive material relative to other materials typically within the same test group of materials. The relative speed values are not absolute speed values. However, relative speed values are related to absolute speed values. The relative electrical speed (shoulder or toe speed) is obtained simply by arbitrarily assigning a value, Ro, to one particular shoulder or to speed of one particular photoconductive material. The relative shoulder or toe speed, Rn, of any other photoconductive material, n, relative to this value, Ro, may then be calculated as follows: $Rn=(A_n)$-(Ro/Ao) wherein An is the absolute electrical speed of the first material. The absolute H & D electrical speed, either the shoulder (SH) or toe speed, of a material may be determined as follows: The material is electrostatically charged under, for example, a corona source until the surface potential, as measured by an electrometer probe, has an initial value $V_o$, of about 600 volts. The charged element is then exposed to a 3000° K. tungsten light source through a stepped density gray scale. The exposure causes reduction of the surface potential of the element under each step of the gray scale from its initial potential $V_o$ to some lower potential V the exact value of which depends upon the amount of exposure in meter-candle-seconds received by the area. The results of these measurements are then plotted on a graph of surface potential V vs. log exposure for each step, thereby forming an electrical characteristic curve. The electrical or electrophotographic speed of the photoconductive composition can then be expressed in terms of the reciprocal of the exposure required to reduce the surface potential to any fixed selected value. The actual positive or negative shoulder speed is the numerical expression of $10^4$ divided by the exposure in meter-candle-seconds requied to reduce the initial surface potential $V_o$ to some value equal to $V_o$ minus 100. This is referred to as the 100 volt shoulder speed. Sometimes it is desirable to determine the 50 volt shoulder speed and, in that instance, the exposure used is that required to reduce the surface potential to $V_o$ minus 50. Similarly, the actual positive or negative toe speed is the numerical expression of $10^4$ divided by the exposure in meter-candle-seconds required to reduce the initial potential $V_o$ to an absolute value of 100 volts. Again, if one wishes to determine the 50 volt toe speed, one merely uses the exposure required to reduce $V_o$ to an absolute value of 50 volts. An apparatus useful for determining the electrophotographic speeds of photoconductive compositions is described in Robinson et al, U.S. Pat. No. 3,449,658, issued June 10, 1969.

TABLE 3

| Compound (From Table I) | Relative Electrical Speed: Organic Photo-conductor | Positive Shoulder | Positive Toe | Negative Shoulder | Negative Toe |
|---|---|---|---|---|---|
| control | A | 231 | 0 | 74 | 0 |
| control | B | 100* | 0 | 95 | 0 |
| 12 | A | 3314 | 126 | 2104 | 84 |
| | B | 4471 | 210 | 2630 | 105 |
| 17 | A | 1578 | 58 | 1525 | 58 |
| | B | 3313 | 152 | 1999 | 79 |
| 18 | A | 1683 | 53 | 1052 | 26 |
| | B | 2630 | 84 | 2104 | 142 |
| 20 | A | 2314 | 95 | 1683 | 74 |
| | B | 6312 | 263 | 2630 | 131 |
| 25 | A | 2630 | 147 | 1894 | 84 |
| | B | 3314 | 210 | 2667 | 152 |

*Arbitrarily assigned a value of 100
This series of photoconductive insulating compositions shows that the heterocyclic pyrylium dye salts of the present invention enhance the sensitivity of organic photoconductors in the visible region of the spectrum.

EXAMPLE 2

A dye-first dope is prepared according to the method disclosed in U.S. Pat. No. 3,615,396:

| | |
|---|---|
| poly[4,4'-(2-norbornylidene) diphenyl carbonate] | 0.375 g |
| Tri-p-tolylamine photoconductor | 0.25 g |
| Compound 2 of Table 1 | 0.013 g (2.08%) |
| Methylene dichloride | 3.8 ml |

This dope is coated on a conductive support and dried. A portion of the magenta-colored, homogeneous layer was overcoated with toluene to form a blue, aggregated layer. Samples of the homogeneous and aggregated materials were tested providing the following data:

| Coating | Color | $D_{min}$ | $D_{max}$ | Relative Speed (−500V/250V) ergs/cm² 500nm | 600nm |
|---|---|---|---|---|---|
| Homogeneous | Magenta | 455nm | 545nm | 1.0* | 1.07 |
| Aggregated | Blue | 455nm | 630nm | 0.37 | 0.43 |

*Arbitrarily assigned a value of 1.0.

This example shows that compound 2 results in photoconductive materials having absorbance in the blue region of the visible spectrum as well as at longer wavelengths well within visible spectrum. Absorption at longer wavelengths well within the visible spectrum makes available aggregate photoconductive compositions which are more panchromatic than prior art aggregate photoconductive compositions.

EXAMPLE 3

Compounds 12, 17, 18, 19, 20, 25 and 26 were each separately aggregated according to the dye first technique disclosed in U.S. Pat. No. 3,615,396. The resulting photoconductive compositions included the following components:

| | |
|---|---|
| Lexan ® 145 (Bisphenol A Polycarbonate sold by General Electric Co.) | 1.0 gm |
| Compound from Table I | 0.2 gm |
| Methylene Chloride Solvent | 5.4 ml |

Each composition was coated on a conductive polyester film support. The optical density of each coated composition was determined and plotted against wavelength. Each coated composition was then fumed and optical density again determined and plotted against wavelength. Density determinations and microscopic examinations confirm that each of the tested compounds formed aggregate photoconductive compositions.

The aggregate compositions utilizing the heterogeneous pyrylium dye salts of this invention generally exhibit enhanced absorption and sensitivity compared to aggregate compositions disclosed in Light, U.S. Pat. No. 3,615,414 and Gramza et al U.S. Pat. No. 3,732,180. Another feature of the present invention is that it provides the means to selectively fill absorption "holes" or "windows" which may be present within the visible absorption spectra of conventional aggregate materials. This is accomplished by using a heterocyclic pyrylium type dye salt with the appropriate absorption characteristics to fill-in or enhance absorption in a particular region of the visible spectrum. For example, compounds 17, 18, 19, 20, 25 and 26 of Example 3 have absorption peaks in the blue region of the visible spectrum. Hence they are extremely useful in eliminating the blue void which occurs in the prior art aggregate composition mentioned above.

This feature of the invention is also exemplified in Example 4 wherein the heterocyclic pyrylium dye salts of the present invention are used in combination with conventional pyrylium dye salts to form aggregate photoconductive compositions.

The basic formulation for Examples 4–6 is:
Binder: Lexan 145, Polycarbonate (60 parts by weight)
Organic Photoconductor: 4,4'-Bis(diethylamino)-2,2'-dimethyltriphenylmethane (40 parts by weight)
Combination of Pyrylium Dye Salts: (3 parts by weight)

Table I compound was combined with 4-(4-dimethylaminophenyl)-2,6-diphenylthiopyrylium tetrafluoroborate utilized as the conventional pyrylium dye salt. The combined concentration of the conventional pyrylium dye salt and the compound from Table I was held to 3 parts by weight of the total formulation.

These formulations were aggregated according to the dye first techniques of U.S. Pat. No. 3,615,396. The formulations were coated from 15% solids in a 60/40 dichloromethane/1,1,2-trichloroethane solvent mixture at a 10 micron dry coverage on a subbed 0.40 OD nickelized poly(ethylene terephthalate) film support. After drying the coatings were cured for 4 hours at 60° C. to remove all residual solvent.

EXAMPLE 4

An aggregate photoconductor material corresponding to the basic formulation including 2.25 parts of 4-(4-dimethylaminophenyl)-2,6-diphenylthiopyrylium tetrafluoroborate and 0.75 parts of 2,6-di(2-thienyl)-4-(4-dimethylaminophenyl)thiopyrylium perchlorate (compound 19) showed an absorption of 0.8 at 460 nm. When compound 19 is omitted from this formulation the absorption at 460 nm is about 0.4. Wedge spectrograms in both the positive and negative charging modes exhibited a substantially panchromatic response between 400 and 700 nm.

EXAMPLE 5

An aggregate photoconductive composition was prepared according to example 4 except that the concentration of compound 19 and the conventional dye were both maintained at 1.5 parts by weight of the total composition. Sensitivity measurements were made and it was found that the sensitivity of this composition was substantially greater than a similar composition in which compound 19 is omitted.

It will be apparent from the foregoing examples and description that the compositions of the present invention can be used in electrophotographic elements having many stuctural variations. For example, the photoconductive composition can be coated in the form of single layers or multiple layers on a suitable opaque or transparent conducting support.

The invention has been described in detail with particular reference to certain preferred embodiments thereof, but it will be understood that variations and modifications can be effected within the spirit and scope of the invention.

We claim:

1. A 2,4,6-trisubstituted pyrylium dye salt having the structure:

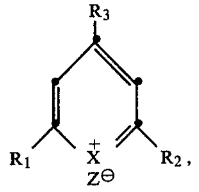

wherein:

each of $R_1$ and $R_2$, which may be the same or different, represent a phenyl radical, thienyl, furyl, pyridyl, pyrrolyl, pyrimidinyl, thiadiazolyl or thiazolyl, with the proviso that no more than one of $R_1$ and $R_2$ is a phenyl radical;

$R_3$ represents an alkylamino-substituted phenyl radical, dialkylaminopyridyl, dialkylaminofuryl, dialkylaminothienyl, dialkylaminopyrimidinyl, dialkylaminothiadiazolyl or dialkylaminothiazolyl;

X represents oxygen or sulfur;

Z represents an anion and wherein at least one of $R_1$, $R_2$ and $R_3$ is one of the above enumerated heterocyclic moieties.

2. A 2,4,6-trisubstituted pyrylium dye salt according to claim 1 in which X is sulfur.

3. A 2,4,6-trisubstituted pyrylium dye salt according to claim 1 in which $R_1$ and $R_2$ represent phenyl, 2-thienyl, 3-thienyl, 2-furyl, 2-pyridyl, 3-pyridyl, 4-pyridyl, or 3-pyrrolyl; $R_3$ represents 4-dimethylaminophenyl, or 4-dimethylamino-3-pyridyl; X represents oxygen or sulfur and Z represents hexafluorophosphate, fluoroborate or perchlorate.

4. A 2,4,6 trisubstituted pyrylium dye salt according to claim 1 in which $R_1$ and $R_2$ represent phenyl, 2-thienyl, 3-thienyl, 2-furyl, 2-pyridyl, 3-pyridyl, 4-pyridyl, 3-pyrrolyl, 2-pyrimidinyl, 1,3,4-thiadiazol-2-yl or 2-thiazolyl; $R_3$ represents 4-dimethylaminophenyl, 4-dimethylamino-3-pyridyl or 5-dimethylamino-2-thienyl; X represents sulfur and Z is hexafluorophosphate, fluoroborate or perchlorate.

5. A 2,4,6-trisubstituted pyrylium dye salt according to the formula of claim 2 wherein the compound is 4-(4-dimethylaminophenyl)-2-phenyl-6-(2-thienyl)thiopyrylium fluoroborate; 4-(4-dimethylaminophenyl)-2-phenyl-6-(2-thienyl)thiopyrylium perchlorate; 2-(2-thienyl)-4-(4-dimethylaminophenyl)-6-(3-thienyl)thiopyrylium fluoroborate; 4-(4-dimethylaminophenyl)-2-(2-furyl)-6-phenylthiopyrylium perchlorate; 2-(3-pyridyl)-4-(dimethylaminophenyl)-6-(2-thienyl)thiopyrylium perchlorate; 2,6-di-(2-furyl)-4-(4-dimethylaminophenyl)thiopyrylium perchlorate; 4-(4-dimethylaminophenyl)-2,6-di-(2-thienyl)thiopyrylium perchlorate; 2,6-di-(2-thienyl)-4-(4-dimethylaminophenyl)-pyrylium fluoroborate; 4-(4-dimethylaminophenyl)-2-phenyl-6-(2-pyrimidinyl)thiopyrylium perchlorate; 4-(4-dimethylaminophenyl)-2-phenyl-6-(1,3,4-thiadiazol-2-yl)thiopyrylium perchlorate; 4-(4-dimethylamino-phenyl)-2-phenyl-6-(2-thiazolyl)thiopyrylium perchlorate or 4-(4-dimethylaminophenyl)-2-phenyl-6-(3-pyrrolyl)-thiopyrylium perchlorate.

* * * * *